(12) United States Patent
Da Rocha Costa

(10) Patent No.: US 8,609,021 B2
(45) Date of Patent: Dec. 17, 2013

(54) METHOD FOR DISINFECTING A ROOM AND OBJECTS CONTAINED THEREIN AND DISINFECTING COMPOSITION

(75) Inventor: Aline Maria Da Rocha Costa, Rio de Janeiro (BR)

(73) Assignee: 99 Holding S.A.R.L., Luxembourg (LU)

( * ) Notice: Subject to any disclaimer, the term of this patent is extended or adjusted under 35 U.S.C. 154(b) by 407 days.

(21) Appl. No.: 12/999,591

(22) PCT Filed: Jun. 26, 2009

(86) PCT No.: PCT/IB2009/052767
§ 371 (c)(1),
(2), (4) Date: Dec. 16, 2010

(87) PCT Pub. No.: WO2010/001319
PCT Pub. Date: Jan. 7, 2010

(65) Prior Publication Data
US 2011/0104005 A1    May 5, 2011

(30) Foreign Application Priority Data
Jun. 30, 2008  (IT) .............................. BO2008A0418

(51) Int. Cl.
*A61L 9/00* (2006.01)
*A62B 7/08* (2006.01)
*A61L 9/04* (2006.01)
*A61L 9/01* (2006.01)

(52) U.S. Cl.
USPC ............ 422/5; 422/1; 422/4; 422/28; 422/37; 422/34; 422/123; 422/124; 422/125; 424/405; 424/76.2; 424/76.3; 424/76.8; 252/186.43

(58) Field of Classification Search
USPC ........... 422/1, 4–5, 28, 37, 34, 123–125, 292, 422/298, 305–306; 424/405, 76.2, 76.3, 424/76.8; 252/186.1, 186.43
See application file for complete search history.

(56) References Cited

U.S. PATENT DOCUMENTS

| | | | |
|---|---|---|---|
| 6,277,414 B1 * | 8/2001 | Elhaik et al. .................. 424/616 |
| 6,797,302 B1 | 9/2004 | Yehuda et al. | |
| 2004/0005240 A1 | 1/2004 | Adiga et al. | |
| 2006/0008379 A1 | 1/2006 | Mielnik et al. | |
| 2006/0280665 A1 | 12/2006 | Rees et al. | |
| 2007/0125882 A1 | 6/2007 | Schwal et al. | |
| 2007/0190172 A1 | 8/2007 | Bobbert | |
| 2010/0233020 A1 | 9/2010 | Klaassen et al. | |

FOREIGN PATENT DOCUMENTS

| | | |
|---|---|---|
| EP | 1100341 A1 | 5/2001 |
| FR | 2860721 | 4/2005 |
| WO | 2005025757 A2 | 3/2005 |
| WO | WO 2007/125100 A1 * | 8/2007 |
| WO | 2007125100 A1 | 11/2007 |

* cited by examiner

*Primary Examiner* — Monzer R Chorbaji
(74) *Attorney, Agent, or Firm* — Pearne & Gordon LLP

(57) ABSTRACT

The present invention relates to a method for disinfecting a room and the objects that may be contained therein, or surfaces in general, including the following steps: (a) determining the volume of the room to be disinfected; (b) as a function of the value determined in step a) above, determining a volumetric concentration of an aqueous disinfecting solution delivered into the room in the form of a dry mist required for obtaining a predefined level of disinfection, said disinfecting solution comprising hydrogen peroxide and silver ions ($Ag^+$); (c) delivering into the room said aqueous disinfecting solution in the form of a dry mist until the desired volumetric concentration is achieved; (d) keeping said aqueous disinfecting solution in the form of a dry mist in contact with the room and with the objects that may be contained therein for a predefined time, so as to achieve a desired level of disinfection. A second object of the present invention consists in a disinfecting solution that is particularly suitable for implementing said method.

20 Claims, No Drawings

METHOD FOR DISINFECTING A ROOM AND OBJECTS CONTAINED THEREIN AND DISINFECTING COMPOSITION

TECHNICAL FIELD

The present invention relates to a method for disinfecting a room and the objects contained therein and to a disinfecting composition that is particularly suitable for implementing said method. More specifically, the present invention relates to a method for disinfecting a room and the objects contained therein, or surfaces in general, in particular of sanitary rooms, such as for instance laboratories, health care centers, hospital rooms, ambulance compartments, etc., and medical devices placed e.g. inside a disinfecting chamber, using an aqueous disinfecting solution based on hydrogen peroxide which is delivered into rooms in the form of a dry mist.

STATE OF THE ART

In the field of disinfection of sanitary rooms about the use of aqueous solutions based on hydrogen peroxide is already known.

An example of the state of the art is disclosed in European patent application EP 1 100 341 A1, relating to a method and a composition for treating vegetable and food products for preventing the deterioration thereof, which can also be used for eliminating or reducing the amount of harmful organisms in farmlands, water and also working areas, surfaces etc. The method includes the use of an aqueous solution comprising: hydrogen peroxide in a concentration of 0.001% to 50%; dispersed metals or metal ions in an amount of 1 ppb to 5% with an effective concentration of metal ions, selected among copper, zinc, nickel, iron, manganese, molybdenum, potassium and mixtures thereof, of 2.5% or lower, and an effective concentration of silver ions of 2.5% of lower, as well as optional addition of various additives, such as hydrogen peroxide activators, hydrogen peroxide stabilizers or modifiers, pH adjusters or organic and/or inorganic additives.

Another example of known technique is the system known as Nocolyse-Nocospray, which makes use of an aqueous solution based on hydrogen peroxide with bactericide, antiviral and fungicide activity, sprayed and delivered into a room using a delivery device which, by means of Venturi effect, enables to produce an extremely large number of product microbubbles, thus hugely increasing the contact surface and promoting the generation by hydrogen peroxide of oxidizing compounds that are able to destroy microorganisms.

French patent application published as FR 2 860 721 (issued to Gloster Sante Europe) describes a process for treating a room by delivering a disinfecting liquid into the room atmosphere, wherein the delivery into the room occurs according to a well defined operating sequence so as to deliver into each room a sufficient liquid dose so as to obtain an effective treatment, without exceeding the toxicity and allergenicity limits of the product, depending on the volume of the room to be treated. An important aim of this method is to keep in time traceability of the type and amount of product used for treating every room. Such method basically includes the following steps: a) arranging a disposable container for liquid, provided with liquid identifier, on a device equipped with a reader for said identifier; b) reading said identifier by means of said reader; c) checking the compliance of said product identifier and comparing the reading with a list of identifiers of suitable products; d) making a hole in said container for enabling liquid delivery; e) determining the amount of said liquid to be delivered into the room; f) delivering said amount of liquid into the room; g) recording in a memory of said device the identifier and the amount of delivered liquid.

For the delivery of the disinfecting liquid solution, several devices are known in the art and on the market for disinfecting methods known as Nocolyse-Nocospray as already referred to above, and also "Sterinis" by the French company Gloster Sante Europe, owner of international patent application WO 2005/025757 relating to an atomizer of liquid substances wherein, in order to obtain an optimal atomization of the liquid substance, a device with an ultrasound vibration effect is used, arranged downstream from a pair of devices with Venturi effect.

DESCRIPTION OF THE INVENTION

The Applicant has performed studies in order to achieve an optimal disinfection of any kind of surfaces in rooms, especially hospital rooms, laboratories, ambulance compartments etc., or of medical devices, and has found that with known techniques product doses that do not often meet actual operating needs have to be used, e.g. too high doses of disinfecting liquid if compared with real needs, or insufficient doses with respect to the room to be treated and to the specific sanitization to be carried out.

Experimentally, the Applicant has been able to find that, after determining the volume of the room to be treated, it is possible to determine the volumetric concentration of the disinfecting solution (i.e. the amount of disinfecting solution delivered with respect to the volume of the room to be treated) required for obtaining the desired disinfection of the room and of the objects contained therein (appliances, pieces of furniture, etc.) without any moist residue of the solution delivered into the room.

A first object of the present invention therefore consists in a method for disinfecting a room and the objects that may be contained therein, including the following steps:
 (a) determining the volume of the room to be disinfected;
 (b) as a function of the value determined in step a) above, determining a volumetric concentration of an aqueous disinfecting solution delivered into the room in the form of dry mist required for obtaining a predefined level of disinfection, said disinfecting solution comprising hydrogen peroxide and silver ions ($Ag^+$);
 (c) delivering into the room said aqueous disinfecting solution in the form of dry mist until the desired volumetric concentration is achieved;
 (d) keeping said aqueous disinfecting solution in the form of dry mist in contact with the room and with the objects that may be contained therein for a predefined time, so as to achieve a desired level of disinfection.

In a preferred embodiment of said method, said step (b) is also preceded by a step (a') of determining the type and degree of microorganism contamination of the room. This enables to define even more accurately the volumetric concentration of an aqueous disinfecting solution required according to step (b).

A second object of the present invention consists of a disinfecting solution that is particularly suitable for implementing said method.

Said aqueous disinfecting solution comprises:
 (a) 2 to 30% by weight of hydrogen peroxide;
 (b) 20 to 140 mg/kg of silver ions ($Ag^+$);
 (c) 10 to 250 mg/kg of phosphate and/or hydrogen phosphate ions;
 (d) 0.1 to 2 g/kg of at least one non-ionic surfactant.

A particularly preferred aqueous disinfecting solution comprises:
- (a) 3 to 10% by weight of hydrogen peroxide;
- (b) 40 to 120 mg/kg of silver ions ($Ag^+$);
- (c) 20 to 200 mg/kg of phosphate and/or hydrogen phosphate ions;
- (d) 0.1 to 2 g/kg of at least one non-ionic surfactant.

A particularly preferred aqueous disinfecting solution is also the following:
- (a) 5 to 30% by weight of hydrogen peroxide;
- (b) 20 to 100 mg/kg of silver ions ($Ag^+$);
- (c) 10 to 40 mg/kg of phosphate and/or hydrogen phosphate ions;
- (d) 0.1 to 2 g/kg of at least one non-ionic surfactant.

Another preferred aqueous disinfecting solution is the following:
- (a) 10 to 20% by weight of hydrogen peroxide;
- (b) 30 to 60 mg/kg of silver ions ($Ag^+$);
- (c) 15 to 30 mg/kg of phosphate and/or hydrogen phosphate ions;
- (d) 0.1 to 2 g/kg of at least one non-ionic surfactant.

As far as the concentration of hydrogen peroxide is concerned, this is expressed as % by weight with respect to the weight of the final solution, whereas the concentration of the other components is expressed as amount by weight (mg or g) with respect to the weight (kg) of the final solution.

A further object of the present invention consists in the use of an aqueous disinfecting solution as defined above for disinfecting a room and the objects that may be contained therein by delivering the solution in the form of a dry mist.

Preferably, silver ions are added in the form of soluble salts. Silver nitrate ($AgNO_3$) is particularly preferred. It is believed that the presence of nitrate ions promotes the stability of hydrogen peroxide and also inhibits the corrosion of metal materials with which the disinfecting solution may come into contact. The silver ions present in the aqueous disinfecting solution according to the present invention can also derive from the addition of silver salts different from $AgNO_3$, in particular $Ag_2SO_4$.

As far as phosphate and/or hydrogen phosphate ions are concerned, these can be introduced into the disinfecting solution by addition of a water-soluble phosphate and/or hydrogen phosphate, in particular $KH_2PO_4$, or by addition of phosphoric acid $H_3PO_4$. It is believed that phosphate and/or hydrogen phosphate ions have a stabilizing effect for hydrogen peroxide. In particular, it is believed that the introduction of said ions enables an optimal pH adjustment with the formation of a buffered solution with acid pH, with such a value that hydrogen peroxide is more stable and has a particularly high oxidizing power.

The aqueous disinfecting solution according to the present invention can include, if necessary, in addition to phosphate and/or hydrogen phosphate ions, at least one complex phosphate or phosphonate in an amount of 0 to 300 mg/kg. Said at least one complex phosphate or phosphonate can be selected e.g. among: potassium pyrophosphate, sodium orthophosphate, sodium tripolyphosphate, sodium hexametaphosphate, sodium hydroxyethylidendiphosphonate and analogs, and mixtures thereof.

As far as said at least one non-ionic surfactant is concerned, this is selected among those having a proven resistance to hydrogen peroxide, preferably among: ethoxylated fatty alcohols, ethoxylated fatty acids, esters of ethoxylated fatty acids, or mixtures thereof, preferably having an ethoxylation degree of 7 to 30. It is believed that the presence of said at least one non-ionic surfactant promotes the spraying process for the disinfecting solution.

The disinfecting solution according to the present invention can further comprise, if necessary, ions of other metals known for their biocide properties, in particular copper ions and/or zinc ions.

Preferably, the disinfecting solution according to the present invention is substantially free of chloride ions. It is indeed believed that chloride ions, beyond inhibiting the action of silver ion, with which they form a highly insoluble compound, can promote corrosion phenomena on the metal surfaces with which the disinfecting solution can come into contact, in particular the parts of the spraying device such as outlet nozzles.

On the basis of the experiments carried out by the Applicant, it has been found that the volumetric concentration of the disinfecting solution in the form of dry mist is preferably in the range from 1 to 30 ml/m$^3$, more preferably from 5 to 15 ml/m$^3$.

Preferably, the dry mist of disinfecting solution consists of microdroplets with an average size below 5 μm, preferably below 3 μm.

The step of delivery of the disinfecting solution into the room so as to obtain a dry mist, can be carried out with a spraying device known in the art, as disclosed, for example in the introductory part.

Preferably, the delivery rate is of 70 m/sec to 90 m/sec, preferably above 80 m/sec. The pressure is selected so as to obtain the delivery of the disinfecting solution in the form of a dry mist at a temperature of from 35° C. to 40° C.

As far as (d) step is concerned, the contact time of the disinfecting solution with the room to be disinfected is generally in the range from 5 minutes to 20 minutes, preferably from 10 minutes and 15 minutes.

As far as the determination of the type and degree of contamination of the room to be disinfected and of the effectiveness of the disinfecting treatment is concerned, this can be based on well-known methods of culture of the microorganisms taken into consideration, so as to carry out a count of vital microorganisms expressed as CFU/cm$^2$.

The effectiveness of the disinfecting treatment can be evaluated by means of vitality reduction (R):

$$R = \frac{N_V}{N_A}$$

wherein:
$N_V$=CFU on sample surface before treatment;
$N_A$=CFU on sample surface after treatment.

The invention claimed is:

1. A method for disinfecting a room and the objects that may be contained therein, including the following steps:
   - (a) determining the volume of the room to be disinfected;
   - (b) as a function of the value determined in step a) above, determining a volumetric concentration of an aqueous disinfecting solution delivered into the room in the form of a dry mist required for obtaining a predefined level of disinfection, said disinfecting solution comprising hydrogen peroxide and silver ions ($Ag^+$);
   - (c) delivering into the room said aqueous disinfecting solution in the form of a dry mist until the desired volumetric concentration is achieved;
   - (d) keeping said aqueous disinfecting solution in the form of a dry mist in contact with the room and with the objects that may be contained therein for a predefined time, so as to achieve a desired level of disinfection, wherein said aqueous disinfecting solution comprises:

(a) 2 to 30% by weight of hydrogen peroxide;
(b) 20 to 140 mg/kg of silver ions (Ag$^+$);
(c) 10 to 250 mg/kg of phosphate and/or hydrogen phosphate ions;
(d) 0.1 to 2 g/kg of at least one non-ionic surfactant selected from: ethoxylated fatty alcohols, ethoxylated fatty acids, esters of ethoxylated fatty acids, or mixture thereof.

2. The method according to claim 1, further including, before step (b), the step of:
(a') determining the type and degree of microorganism contamination of the room, as a function of which step (b) can be carried out.

3. The method according to claim 1, wherein the volumetric concentration of the disinfecting solution in the form of dry mist is in the range from 1 to 30 ml/m$^3$.

4. The method according to claim 1, wherein the dry mist of disinfecting solution consists of microdroplets with an average size below 5 μm.

5. The method according to claim 1, wherein the step of delivery of the disinfecting solution into the room is carried out with a spraying device having a delivery rate in the range from 70 m/sec to 90 m/sec, and with a pressure, measured on the outlet nozzle, selected so as to obtain the delivery of the disinfecting solution in the form of a dry mist at a temperature of from 35° C. to 40° C.

6. The method according to claim 1, wherein during step (d) the contact time of the disinfecting solution in the form of dry mist with the room to be disinfected is of 5 minutes to 20 minutes.

7. The method according to claim 1, wherein the disinfecting solution is an aqueous disinfecting solution comprising:
(a) 2 to 30% by weight of hydrogen peroxide;
(b) 20 to 140 mg/kg of silver ions (Ag$^+$);
(c) 10 to 250 mg/kg of phosphate and/or hydrogen phosphate ions;
(d) 0.1 to 2 g/kg of at least one non-ionic surfactant.

8. An aqueous disinfecting solution comprising:
(a) 2 to 30% by weight of hydrogen peroxide;
(b) 20 to 140 mg/kg of silver ions (Ag$^+$);
(c) 10 to 250 mg/kg of phosphate and/or hydrogen phosphate ions;
(d) 0.1 to 2 g/kg of at least one non-ionic surfactant selected from: ethoxylated fatty alcohols, ethoxylated fatty acids, esters of ethoxylated fatty acids, or mixture thereof.

9. The aqueous disinfecting solution according to claim 8, comprising:
(a) 3 to 10% by weight of hydrogen peroxide;
(b) 40 to 120 mg/kg of silver ions (Ag$^+$);
(c) 20 to 200 mg/kg of phosphate and/or hydrogen phosphate ions;
(d) 0.1 to 2 g/kg of at least one non-ionic surfactant selected from: ethoxylated fatty alcohols. ethoxylated fatty acids, esters of ethoxylated fatty acids, or mixture thereof.

10. The aqueous disinfecting solution according to claim 8, comprising:
(a) 5 to 30% by weight of hydrogen peroxide;
(b) 20 to 100 mg/kg of silver ions (Ag$^+$);
(c) 10 to 40 mg/kg of phosphate and/or hydrogen phosphate ions;
(d) 0.1 to 2 g/kg of at least one non-ionic surfactant selected from: ethoxylated fatty alcohols, ethoxylated fatty acids, esters of ethoxylated fatty acids, or mixture thereof.

11. The aqueous disinfecting solution according to claim 10, comprising:
(a) 10 to 20% by volume of hydrogen peroxide;
(b) 30 to 60 mg/kg of silver ions (Ag$^+$);
(c) 15 to 30 mg/kg of phosphate and/or hydrogen phosphate ions;
(d) 0.1 to 2 g/kg of at least one non-ionic surfactant selected from: ethoxylated fatty alcohols, ethoxylated fatty acids, esters of ethoxylated fatty acids, or mixture thereof.

12. The disinfecting solution according to claim 8, wherein the silver ions are added in the form of a soluble salt.

13. The disinfecting solution according to claim 8, wherein the phosphate and/or hydrogen phosphate ions are introduced into the disinfecting solution by addition of a water-soluble phosphate and/or hydrogen phosphate.

14. The disinfecting solution according to claim 8, wherein the phosphate and/or hydrogen phosphate ions are introduced into the disinfecting solution by addition of phosphoric acid $H_3PO_4$.

15. The disinfecting solution according to claim 8, further comprising at least one complex phosphate or phosphonate in an amount ranging from 0 to 300 mg/kg.

16. The disinfecting solution according to claim 15, wherein said at least one complex phosphate or phosphonate is selected among: potassium pyrophosphate, sodium orthophosphate, sodium tripolyphosphate, sodium hexametaphosphate, sodium hydroxyethylidendiphosphonate and analogs, and mixtures thereof.

17. The disinfecting solution according to claim 8, wherein said at least one non-ionic surfactant has an ethoxylation degree of 7 to 30.

18. The disinfecting solution according to claim 8, further comprising copper ions and/or zinc ions.

19. The disinfecting solution according to claim 8, said solution being substantially free of chloride ions.

20. A method for disinfecting a room, the objects that may be contained therein, or a medical device by delivering an aqueous disinfecting solution according to claim 8 in the form of a dry mist.

* * * * *